United States Patent [19]
Myers et al.

[11] Patent Number: 5,581,355
[45] Date of Patent: Dec. 3, 1996

[54] FINISH METER FOR DETECTING AND MEASURING A METAL OXIDE COATING THICKNESS ON A SEALING SURFACE OF A GLASS CONTAINER AND METHOD OF USING

[75] Inventors: Ronald T. Myers, Whitehouse; Michael T. Dembicki, Pemberville, both of Ohio

[73] Assignee: Owens-Brockway Glass Container Inc., Toledo, Ohio

[21] Appl. No.: 400,739

[22] Filed: Mar. 8, 1995

[51] Int. Cl.⁶ .......................... G01N 21/90; G01B 11/06
[52] U.S. Cl. ........................................ 356/382; 356/428
[58] Field of Search .................................. 356/382, 428

[56] References Cited

U.S. PATENT DOCUMENTS

| | | | |
|---|---|---|---|
| 3,773,420 | 11/1973 | Conroy | 356/382 X |
| 4,026,414 | 5/1977 | Ellinger | 250/223 B |
| 4,399,357 | 8/1983 | Dorf et al. | 250/223 |
| 4,477,494 | 10/1984 | Ali-Zaidi | 427/255.3 |
| 4,495,558 | 1/1985 | Cath et al. | 364/563 |
| 4,682,105 | 7/1987 | Thorn | 324/230 |
| 4,775,889 | 10/1988 | Yoshida . | |
| 4,904,939 | 2/1990 | Mian | 324/229 |
| 4,929,828 | 5/1990 | Claypool | 280/223 |
| 4,946,228 | 8/1990 | Hsu et al. | 301/37 |
| 5,142,228 | 8/1992 | Kingsbury | 324/230 |
| 5,143,896 | 9/1992 | Harada et al. | 505/1 |

OTHER PUBLICATIONS

Glass Testing Methods from American Glass Research, NO 7-71-B, two pages.

*Primary Examiner*—Vincent P. McGraw

[57] ABSTRACT

A method and finish meter for detecting the presence of and measuring the thickness of a metal oxide coating at multiple locations on a sealing surface of a rim of a glass container. The finish meter includes a sensing head for directing a beam of light from a light source against a container and detecting reflected light and a means for positioning the light against the sealing surface of the glass container such that the longitudinal central axis of the sensing head is substantially perpendicular to the sealing surface of the rim of the glass container.

12 Claims, 5 Drawing Sheets

5,581,355

1

FINISH METER FOR DETECTING AND MEASURING A METAL OXIDE COATING THICKNESS ON A SEALING SURFACE OF A GLASS CONTAINER AND METHOD OF USING

FIELD OF THE INVENTION

This invention relates to a finish meter for detecting and measuring a metal oxide coating thickness on a sealing surface of a glass container and a method of using. More particularly, this invention relates to a finish meter for detecting and measuring the thickness of a tin oxide coating at multiple locations around the top, horizontal sealing surface of the rim of a glass container and a method of using.

BACKGROUND OF THE INVENTION

This invention is concerned with a finish meter for measuring the thickness of a metal oxide coating or film, and in particular, a tin oxide coating on the sealing surface of a glass container. A tin oxide coating or film is formed on the surface of a glass container by passing the container, after exiting from a forming machine and while still hot, through a tunnel while injecting into the tunnel a flow of a tin oxide precursor such as tin tetrachloride. Upon contact of the glass container with the atmosphere in the tunnel, the film or coating of tin oxide is formed over the glass container; which serves as a base to which organic coatings are applied, to protect the glass container from abrasion and preserve the strength of the glass container.

A problem that is present when a tin oxide coating or film is applied to a glass container is that the presence of an excessive amount of tin oxide coating on the rim of a glass container adversely affects the torque removal characteristics of a closure on a filled and capped container. Although various apparatuses are known for detecting the presence of an imperfection in an object in the shape of the rim of the glass container or detecting and measuring the thickness of a tin oxide coating on the sidewalls of the container, or along the neck, bead area, and threads of the container, heretofore apparatuses have not been able to detect and measure the thickness of a tin oxide coating or film on the sealing surface of the glass container due to the mechanical limitations of their construction.

It will be appreciated from the foregoing that there is a significant need for a device for detecting and measuring the thickness of a metal oxide coating or film on the sealing contact surface of a glass container. Accordingly, an object of the present invention is to provide a finish meter for detecting and measuring the thickness of a metal oxide coating or film on the sealing contact surface of a glass container.

SUMMARY OF THE INVENTION

Briefly, according to this invention there is provided a finish meter and method for detecting the presence of and measuring the thickness of a metallic oxide coating at multiple locations on the sealing surface of a rim of a glass container. The method includes providing a finish meter of a type which incorporates a sensing head having a light source that directs the beam of light from a light source against a container and detects reflected light as a technique for detecting the presence of and the thickness of a metallic oxide finish at a location in the path of the beam of light; positioning a glass container adjacent the light source with the longitudinal central axis of the glass container being substantially parallel to the longitudinal central axis of the sensing head; engaging the finish of the glass container by a stop member at a location adjacent the rim of the container to ensure that a centered portion of the rim of suitable thickness will be contacted by the beam of light as the container is turned about its longitudinal central axis relative to the sensing head, notwithstanding any allowable eccentricity in the shape of the container; and turning the container through substantially a complete revolution while detecting the presence of and measuring the thickness of a metallic oxide coating at multiple locations on the rim.

The finish meter for detecting the presence of and measuring the thickness of a metal oxide coating at multiple locations on a sealing surface of a rim of a glass container includes a sensing head of a type which directs a beam of light from a light source against a container and detects reflected light as a technique for detecting the presence of and the thickness of a metal oxide coating at a location in the path of the beam of light; and means for positioning the light source adjacent the horizontal rim of the glass container such that a plane formed by the sealing surface of the rim of the glass container is substantially perpendicular to the longitudinal central axis of the sensing head.

BRIEF DESCRIPTION OF THE DRAWINGS

Further features and other objects and advantages of this invention will become clear from the following detailed description made with reference to the drawings in which.

DESCRIPTION OF THE PREFERRED EMBODIMENTS

Figure 1:
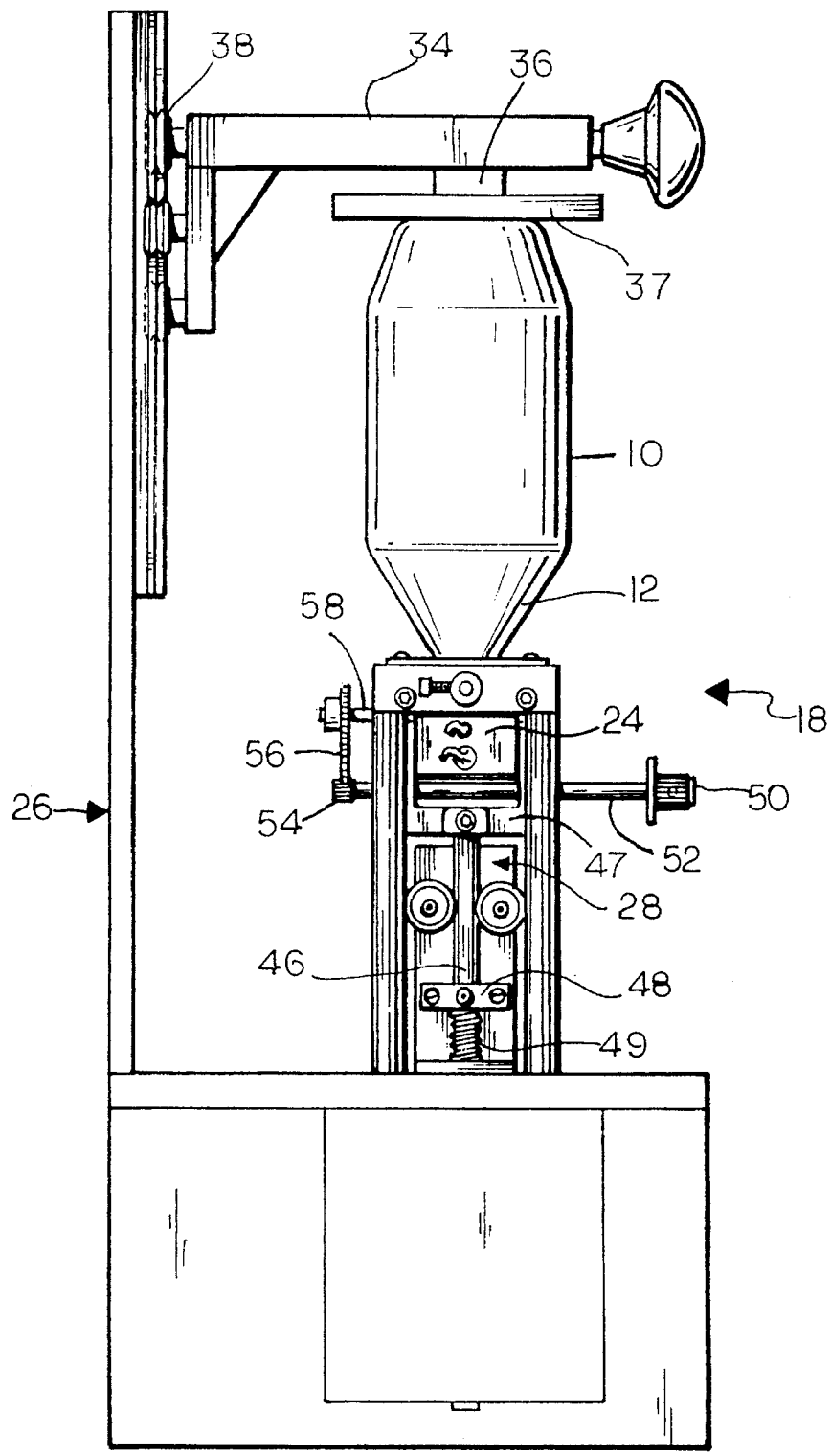
FIG. 1 is a front view of a finish meter in accordance with the present invention for detecting and measuring a metal oxide coating thickness on a sealing surface of a glass container.
Figure 2:
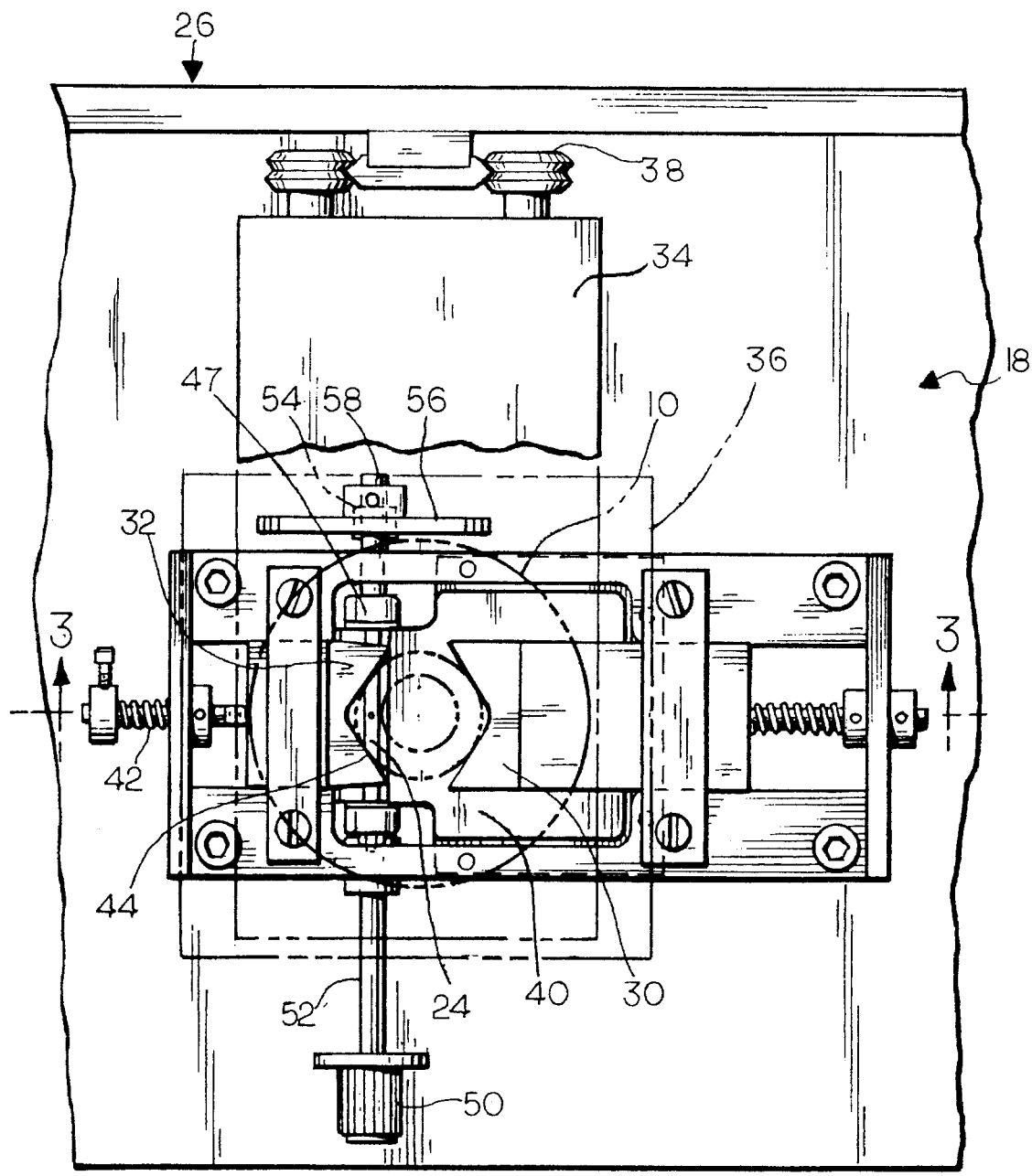
FIG. 2 is a partial sectional top view of the finish meter of FIG. 1.

In the following description, like reference characters designate like or corresponding parts. Also, in the following description, it is to be understood that such terms as "forward", "rearward", "upwardly", "downwardly" and the like are words of convenience and are not to be construed as to imply a necessary positioning of the structure or portions thereof or to limit the scope of this invention.

Figure 3:
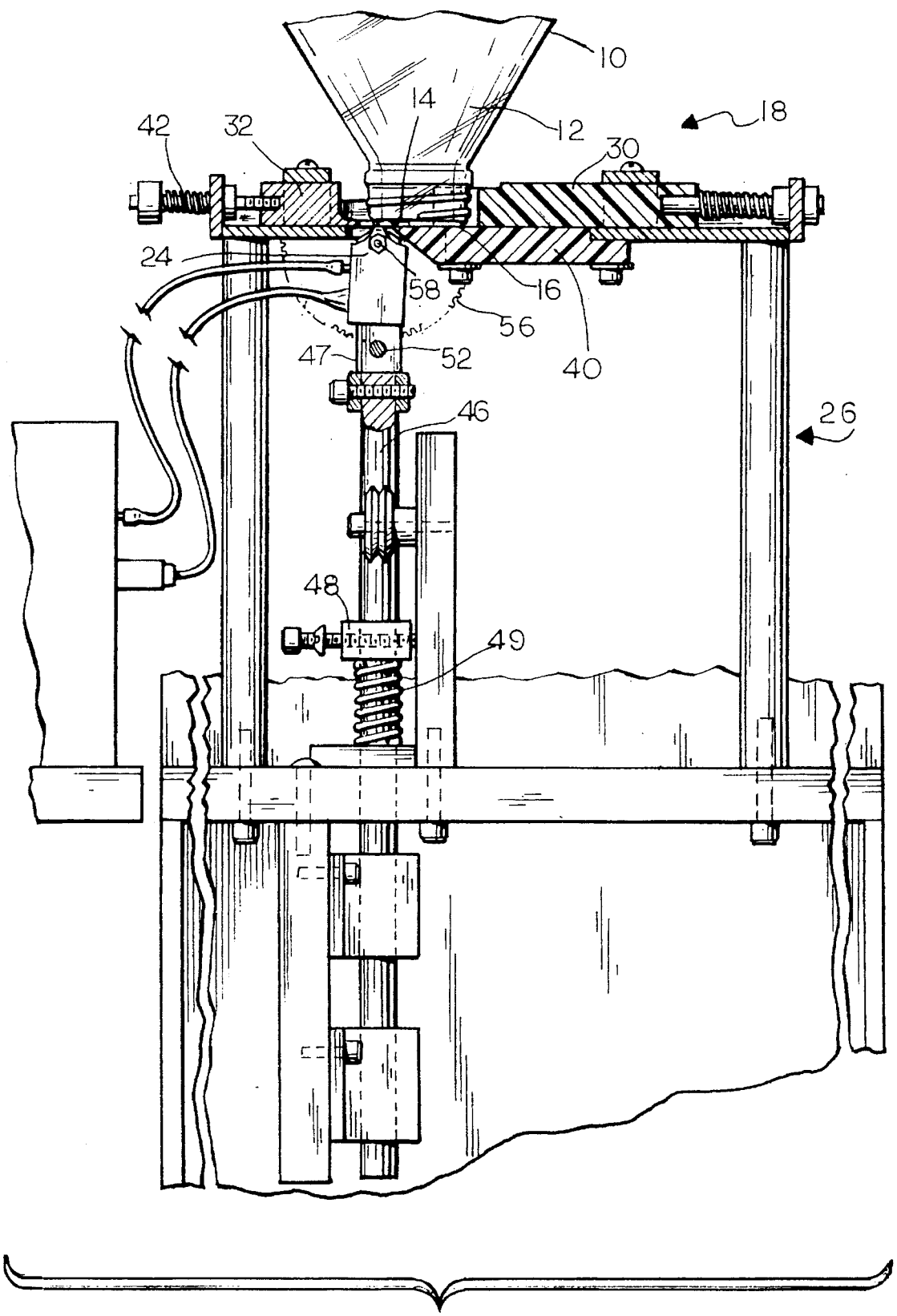
FIG. 3 is a cress-sectional view of the finish meter of FIG. 2 taken along line 3—3.
Figure 4:
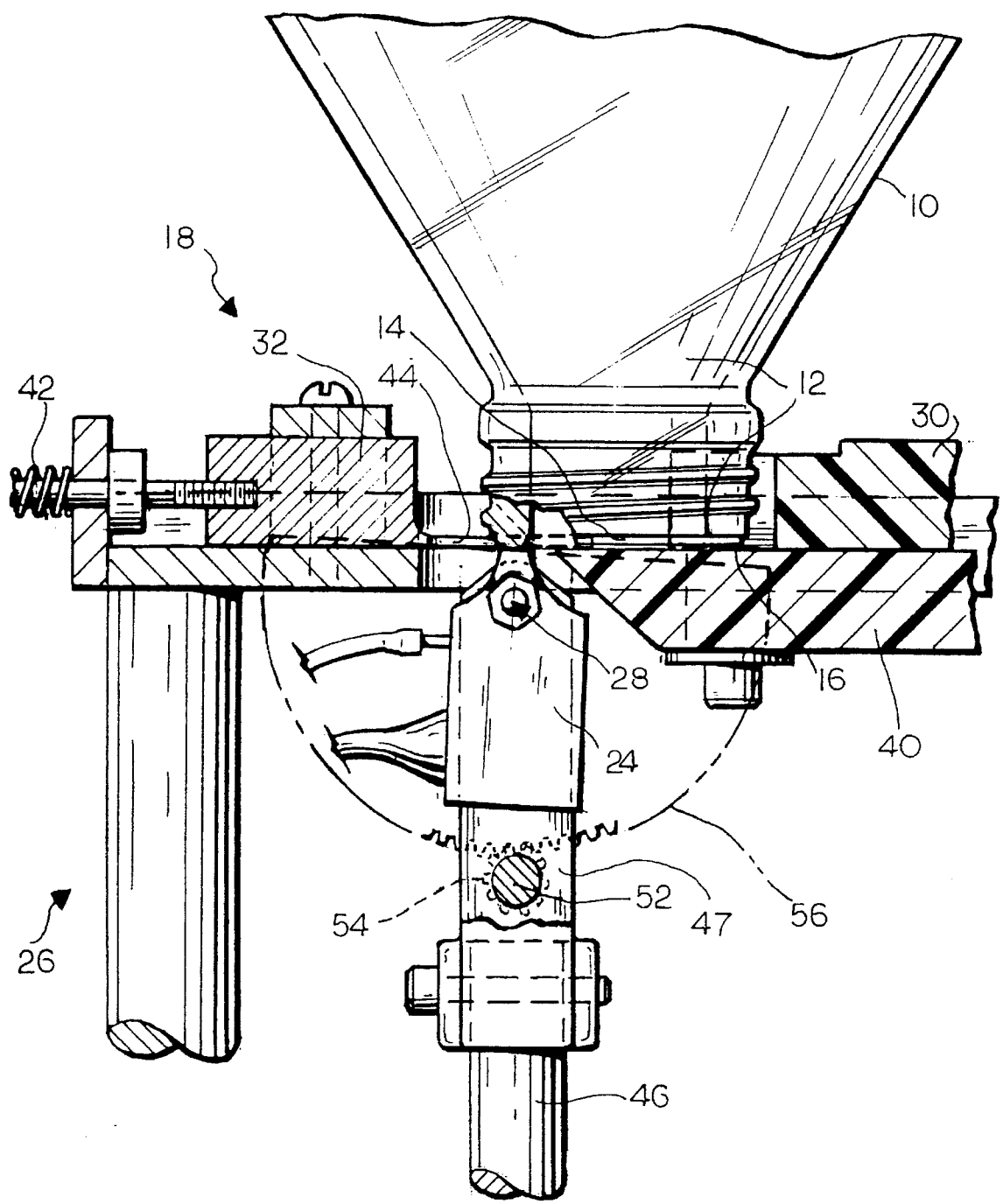
FIG. 4 is an enlarged partial sectional view of the finish meter of FIG. 1.
Figure 5:
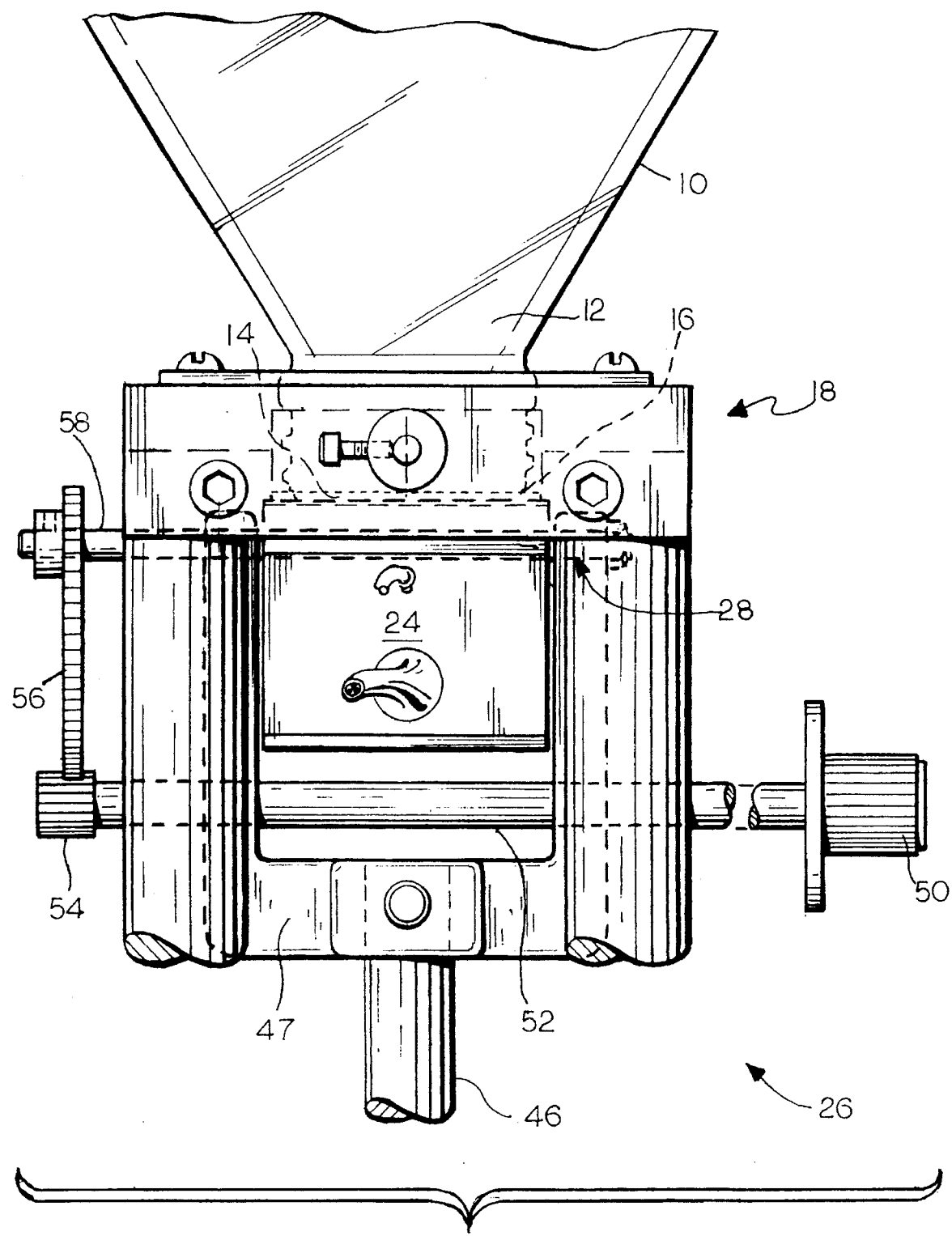
FIG. 5 is an enlarged fragmentary view of the finish meter of FIG. 1.

Referring to the drawings, there is shown a glass container 10 having a metal oxide coating or film 12 such as a tin oxide finish. The glass container 10 may be a carbonated soft drink glass bottle of a type adapted to receive a molded plastic closure (not shown). As shown in FIGS. 3–5, the glass container 10 includes a threaded neck portion or rim defined by a finish guide ring 14 and a sealing surface 16 over which the plastic closure is threaded to provide an air tight seal. The sealing surface 16 of the glass container 10 is generally inclined with respect to a plane formed horizontal to the longitudinal central axis of the glass container. Although a closure will typically provide an acceptable air tight seal with a glass container 10, an excessive amount of metal oxide coating 12 on the sealing surface 16 of the rim of the glass container can adversely affect the torque removal characteristics of the closure on a filled and capped container. The present invention is a finish meter 18 designed for detecting the presence of and the thickness of a metal oxide coating on the sealing surface of a glass container 10. The various components of the finish meter 18, as more fully described herein, may be constructed of most any suitable material as known by one skilled in the art.

The finish meter 18 includes a sensing head 24 and a means for positioning a sensing head having a light source adjacent to and with its central axis perpendicular to the sealing surface 16 of the glass container 10. The glass container 10 is supported in an inverted position and operatively contacts the sensing head 24 to permit a measuring light beam emitted from the sensing head to impinge upon the sealing surface 16 in selected locations around the circumference of the glass container. The sensing head 24 includes a tapered surface to provide sufficient contact with the sealing surface 16 of the glass container 10. The sensing head 24 then detects and measures the light reflected from the metal oxide coating 12 present on the sealing surface 16 as a technique for detecting the presence of and the thickness of the metal oxide coating at the specific location in the path of the beam of light. The sensing head 24 and necessary electronics used in the present invention are of a conventional design and of a type well known in the art. Suitable reflective type meters for detecting and measuring the thickness of a metal oxide coating on the finish may be obtained from American Glass Research, Inc. as well known in the art.

It will be appreciated from the foregoing that the sensing head 24 of the finish meter 18 must necessarily be precisely positioned with respect to the sealing surface 16 to function properly and provide an accurate measure of the thickness of the metal oxide coating 12. In other words, the sensing head 24 must be securely positioned relative to and with its central axis generally perpendicular to the plane formed by the sealing surface 16 of the inverted glass container 10. However, because of the complexity of the geometry and variety of different sealing surfaces 16 available, the sensing head 24 of the finish meter 18 must also be capable of being fixed in a variety of different positions to accommodate a variety of sealing surfaces.

The sensing head 24 of the finish meter 18 is positioned by a glass container mount 26 and a sensing head mount 28. The sensing head mount 28 varies the angle of the sensing head 24 relative to the angle of inclination of the sealing surface 16 of the glass container 10. Similarly, the glass container mount 26 fixes the vertical position of the inverted glass container 10 relative to the finish meter 18.

The glass container mount 26 in accordance with the present invention includes a shoe member 30 and an opposing stop member 32 that surrounds the finish guide ring 14 of the inverted glass container 10 and a vertically sliding back plate 34 having a resilient pad 36 and nylon plate 37 which presses against the bottom of the inverted glass container. The sliding back plate 34 of the glass container mount 26 is movably attached through wheels 38 which travel within a vertical guide track to accommodate glass containers 10 of different heights. The sliding back plate 34 forces the glass container 10 against a bottom plate 40 of the glass container mount 26 between the shoe member 30 and opposing stop member 32 such that the sealing surface 16 is flush against the bottom plate 40. Close contact of the sealing surface 16 and sensing head 24 is assured through the constant downward pressure of the sliding back plate 34 such that the inverted glass container 10 may be rotated to detect the presence of and measure the thickness of a metal oxide coating 12 along the entire sealing surface of the glass container.

It will be appreciated that the sealing surface 16 of the glass container 10 is one of the most important and most precisely formed portions of the glass container in view of the finish contacting and forming a seal with the closure. Although the finish of the glass container 10 may be properly formed, quite often the remainder of the glass container is not. For example, the glass container 10 may be formed such that when the glass container rests on a horizontal surface the longitudinal central axis of the container is not perpendicular to the surface, i.e., the container leans or is tilted. The present invention permits a glass container 10 having a nonperpendicular longitudinal central axis, when properly positioned in the finish meter 18, to be in intimate contact with the bottom plate 40 of the glass container mount 26 as a result of the cooperation of the sliding back plate 34, pad 36 and nylon plate 37 pressing against the base or bottom of the inverted glass container 10. As the inverted glass container 10 is rotated, the pad 36 compensates for the off-level position of the glass container thereby allowing the finish to remain in intimate contact with the bottom plate 40.

The shoe member 30 of the glass container mount 26 is spring loaded to provide constant pressure to force the finish guide ring 14 against the stop member 32. The stop member 32 is operatively connected to a threaded rod or screw 42 which is threaded through a side member of the glass container mount 26 to adjustably vary the distance between the shoe member 30 and stop member to accept glass containers 10 having varying rim diameters and position the sealing surface directly over the sensing head 24 of the meter.

The stop member 32 includes a thin v-shaped edge 44 which contacts the glass container 10 just below a parting line of the finish guide ring 14 to retain the glass container in a fixed position against the shoe member 30. The thickness of the v-shaped edge 44 is machined or formed to contact below the parting line so that the relative position between the top of the finish and the sensing head do not change as the glass container 10 is rotated. The sensing head 24 is sensitive to changes in position such that a change in position of as little as 0.005 in. may cause a gap between the sensing head and the glass container finish 12 thereby effecting the accuracy of any reading from the finish meter 18.

Operatively connected to the glass container mount 26 is the sensing head mount 28. The sensing head mount 28 includes a vertical height adjustment and an angular adjustment. The vertical height adjustment includes a spring loaded yoke 47 movable along a vertical shaft 46 for adjusting the vertical height of the sensing head 24 with respect to the bottom of the plate 40 and the sealing surface 16 and a clamp 48. The clamp 48 tightens against the shaft 46 in a selected vertical position thereby setting the tension of a spring 49 positioned immediately below the clamp. Because the clamp 48 squeezes the shaft 46, the spring 49 pushes against the sensing head 24, the glass container mount 26 and variable angle meter mount 28 such that when a glass container 10 is not positioned in the glass container mount 26, the sensing head 24 presses against the stop member 32.

In a preferred embodiment, the sensing head 24 is an AGR Finish Meter from American Glass Research, Inc. and is machined slightly so that the center portion of the sensing head is capable of extending upward above the "V" shape of the stop member 32. When the glass container 10 is properly positioned, the weight of the glass container 10 and the weight of the sliding back plate 34 are sufficient to press the sensing head 24 downward causing intimate contact between the sensing head and the sealing surface 16.

The angular adjustment of the sensing head 24 permits the sensing head to pivot relative to the sealing surface 16 of the glass container 10 such that the longitudinal central axis of the light source is aligned substantially perpendicular to the sealing surface 16 of the glass container. The angular adjustment of the sensing head 24 is adjusted by manually rotating a control knob 50. The control knob 50 is fixed through a shaft 52 to a gear 54 which meshes with a larger gear 56 pinioned about a second shaft 58. Secured to the second shaft 58 is the sensing head 24. The central axis of the light source is aligned perpendicularly with the sealing surface 16 by manually turning the control knob 50 and causing the gear 54 to rotate the larger gear 56 and pivot the sensing head 24 through an incremental angular displacement. It will be appreciated from the foregoing that the sensing head 24 may be pivoted to detect the presence of and measure the thickness of a metal oxide coating 12 on a variety of different angled sealing surfaces 16 of glass containers 10.

Having described presently preferred embodiments of the present invention, it is to be understood that the invention may be otherwise embodied within the scope of the appended claims.

What is claimed is:

1. A method of detecting the presence of and measuring the thickness of a metal oxide coating at multiple locations on a sealing surface of a rim of a glass container comprising:

providing a finish meter of a type having a sensing head which directs a beam of light from a light source against a container and detects reflected light as a technique for detecting the presence of and the thickness of a metal oxide coating at a location in the path of the beam of light;

positioning a glass container adjacent the light source with the longitudinal central axis of the glass container being substantially parallel to the longitudinal central axis of the sensing head;

engaging the finish of the glass container by a stop member at a location adjacent the rim of the container to ensure that a centered portion of the rim of suitable thickness will be contacted by the beam of light as the container is turned about its longitudinal central axis relative to the sensing head notwithstanding any allowable eccentricity in the shape of the container; and turning the container through substantially a complete revolution while detecting the presence of and measuring the thickness of a metal oxide coating at multiple locations on the sealing surface of the rim.

2. A finish meter for detecting the presence of and measuring the thickness of a metal oxide coating at multiple locations on a sealing surface of a rim of a glass container comprising:

a finish meter of a type having a sensing head which directs a beam of light from a light source against a container and detects reflected light as a technique for detecting the presence of and the thickness of a metal oxide coating at a location in the path of the beam of light; and means for positioning the sensing head adjacent the horizontal rim of the glass container such that a plane formed by the sealing surface of the rim of the glass container is substantially perpendicular to the longitudinal central axis of the sensing head.

3. The finish meter of claim 2 wherein the finish of the rim of the glass container is contacted by the beam of light as the container is turned about its longitudinal central axis relative to the source of light notwithstanding any allowable eccentricity in the shape of the container.

4. The finish meter of claim 3 wherein said positioning means includes a glass container mount and a variable angle meter mount for varying the angle of the sensing head relative to the angle of inclination of the sealing surface of the glass container.

5. The finish meter of claim 4 wherein said glass container mount includes:

a shoe member and an opposing stop member, said shoe member and said stop member cooperatively surround the finish guide ring of the glass container; and a vertically sliding back plate having a resilient pad which presses against the bottom of the glass container.

6. The finish meter of claim 5 wherein said sliding back plate is movably attached through wheels which travel within a vertical guide track to accommodate glass containers of different heights, said sliding back plate capable of forcing the glass container against a bottom plate positioned between said shoe member and said opposing stop member such that the sealing surface is flush against said bottom plate and the glass container may be rotated in position to detect the presence of and measure the thickness of a metal oxide coating along the entire sealing surface.

7. The finish meter of claim 6 wherein said shoe member is spring loaded to provide constant pressure to force the finish guide ring against said stop member.

8. The finish meter of claim 7 wherein said stop member is operatively connected to vary the distance between said shoe member and said stop member to accept glass containers having varying rim diameters and facilitate positioning of said sealing surface directly over said meter.

9. The finish meter of claim 8 wherein said stop member is a thin v-shaped member having an edge which contacts the glass container just below the parting line of the finish guide ring to retain the glass container in a fixed position against the shoe member.

10. The finish meter of claim 9 wherein said meter mount includes a spring loaded yoke for adjusting the vertical height of the sensing head with respect to a bottom of the plate and the sealing surface and a clamp.

11. The finish meter of claim 10 wherein the angular displacement of the meter is adjusted by rotating a control knob fixed through a shaft to a gear which meshes with a larger gear pinioned about a second shaft having secured thereto said finish meter.

12. A finish meter for detecting the presence of and measuring the thickness of a metal oxide coating at multiple locations on a sealing surface of a rim of a glass container comprising:

a finish meter of a type having a sensing head which directs a beam of light from a light source against a container and detects reflected light as a technique for ascertaining the presence of and the thickness of a metal oxide coating at a location in the path of the beam of light; and means for positioning the sensing head adjacent the rim of the sealing surface of the glass container such that the longitudinal central axis of the sensing head is substantially perpendicular to the sealing surface of the rim of the glass container.

\* \* \* \* \*